(12) United States Patent
Talpade

(10) Patent No.: US 6,587,718 B2
(45) Date of Patent: *Jul. 1, 2003

(54) IONTOPHORETIC DELIVERY TO HEART TISSUE

(75) Inventor: Dnyanesh Talpade, Plymouth, MN (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/415,599

(22) Filed: Oct. 8, 1999

(65) Prior Publication Data

US 2002/0055705 A1 May 9, 2002

(51) Int. Cl.⁷ .......................... A61N 1/30; A61M 31/00
(52) U.S. Cl. .......................... 604/21; 604/20; 604/508; 600/374
(58) Field of Search .................. 604/20, 21, 501–2, 604/96.01, 507–9, 48, 93.01, 103.01–103.08, 104–109, 523, 532; 607/119, 120, 122, 129; 600/9, 13–14, 374

(56) References Cited

U.S. PATENT DOCUMENTS

| 5,236,413 | A |   | 8/1993  | Feiring          | 604/21    |
|-----------|---|---|---------|------------------|-----------|
| 5,498,238 | A |   | 3/1996  | Shapland et al.  | 604/21    |
| 5,499,971 | A |   | 3/1996  | Shapland et al.  | 604/53    |
| 5,501,662 | A |   | 3/1996  | Hofmann          | 604/20    |
| 5,507,724 | A |   | 4/1996  | Hofmann et al.   | 604/53    |
| 5,549,603 | A | * | 8/1996  | Feiring          | 604/21    |
| 5,588,961 | A |   | 12/1996 | Leone et al.     | 604/21    |
| 5,669,874 | A | * | 9/1997  | Feiring          | 604/103.01|
| 5,681,278 | A |   | 10/1997 | Igo et al.       |           |
| 5,704,908 | A | * | 1/1998  | Hofmann et al.   |           |
| 5,810,763 | A |   | 9/1998  | Feiring          | 604/20    |
| 5,810,767 | A |   | 9/1998  | Klein            | 604/53    |
| 5,944,710 | A | * | 8/1999  | Dev et al.       | 604/21    |
| 6,055,453 | A | * | 4/2000  | Hofmann et al.   | 604/21    |
| 6,076,012 | A | * | 6/2000  | Swanson et al.   | 604/21    |

FOREIGN PATENT DOCUMENTS

| EP | 0 468 636 A1 | 1/1992  |
|----|--------------|---------|
| EP | 0 882 452 A1 | 12/1998 |
| EP | 0 874 663 B1 | 9/1999  |
| WO | WO 91/16945  | 11/1991 |
| WO | WO 94/05361  | 3/1994  |
| WO | WO 94/05369  | 3/1994  |
| WO | WO 94/22528  | 10/1994 |
| WO | WO 97/49450  | 12/1997 |
| WO | WO 98/06389  | 2/1998  |
| WO | WO 98/15318  | 4/1998  |
| WO | WO 99/04851  | 2/1999  |
| WO | WO 99/06101  | 2/1999  |

OTHER PUBLICATIONS

International Search Report of PCT Application No. PCT/US00/27306 dated Jan. 26, 2000.

* cited by examiner

Primary Examiner—Brian L. Casler
Assistant Examiner—Catherine Serke
(74) Attorney, Agent, or Firm—Westman, Champlin & Kelly, P.A.

(57) ABSTRACT

A therapeutic agent is delivered to heart tissue in a body. The therapeutic agent is introduced to a first side of the heart tissue. An electrode is percutaneously located on a second side of the heart tissue. The electrode is energized to induce migration of the therapeutic agent into the heart tissue.

11 Claims, 8 Drawing Sheets

IONTOPHORETIC DELIVERY TO HEART TISSUE

BACKGROUND OF THE INVENTION

The present invention deals with administering a therapeutic agent, such as a drug. More specifically, the present invention is directed to delivering the therapeutic agent directly to heart tissue in a noninvasive manner.

Iontophoresis can be used to administer a therapeutic agent, such as a drug or other medication or agent. Iontophoresis typically involves an interaction between ionized molecules of a drug (or other therapeutic agent) and an external electric field. This interaction results in the migration of charged molecules. The migration is accomplished by placing two electrodes across the tissue to be treated and charging the electrodes with a relatively low, direct current (DC), voltage. One of the electrodes acts as a source electrode and is typically in contact with the drug solution. The other electrode acts as a return electrode and may be filled with an electrolyte solution. The electric field generated between the two electrodes causes the charged molecules in the therapeutic agent to migrate from one electrode into the tissues to be treated.

This addresses a disadvantage associated with injected therapeutic agents. Iontophoresis tends to diffuse the drug throughout the treated tissue whereas an injection masses a concentrated bolus of drug within the tissue or joint, potentially causing damage to the tissue.

Similarly, delivery of drugs by iontophoresis avoids a disadvantage which comes with oral administration of medication. The disadvantage is known as first-pass metabolism of the drug. When a drug is taken orally and absorbed from the digestive tract into the blood stream, the blood containing the drug first passes through the liver before entering the vasculature where it will be delivered to the tissue to be treated. However, the liver is a metabolically active organ. Thus, much of the orally ingested drug may be metabolically inactivated before it has a chance to exert its pharmacological affect.

Various drug therapies have also been developed to treat coronary disease. Such therapies often require the delivery of drugs, or other treatment material (i.e., a therapeutic agent) to the myocardium, a vessel, or any other organ or area for which transluminal access is desirable. For example, anti-arrythmia drugs may be desirably administered to the myocardium. Similarly, recent advancements and pharmaceutical developments have resulted in gene therapy drugs, such as growth factors, which can be administered to the myocardium for myocardial revascularization. Such therapies have been used in place of, and in conjunction with, other more conventional therapies, such as percutaneous transluminal coronary angioplasty (PTCA), bypass techniques, and atherectory techniques.

SUMMARY OF THE INVENTION

The present invention is drawn to delivering a therapeutic agent (such as a drug or other treatment material) to the myocardium, a vessel, or any other organ or area for which transluminal access is desirable. For example, the present invention can be used to administer anti-arrythmia drugs to the myocardium for electrophysiological therapy. Similarly, growth factors and other gene therapy substances can be administered to the myocardium, using the present invention, for myocardial revascularization.

A therapeutic agent is delivered to heart tissue in a body. The therapeutic agent is introduced to a first side of the heart tissue. An electrode is percutaneously located on a second side of the heart tissue. The electrode is energized to induce migration of the therapeutic agent into the heart tissue.

DETAILED DESCRIPTION OF THE ILLUSTRATIVE EMBODIMENTS

Figure 1:
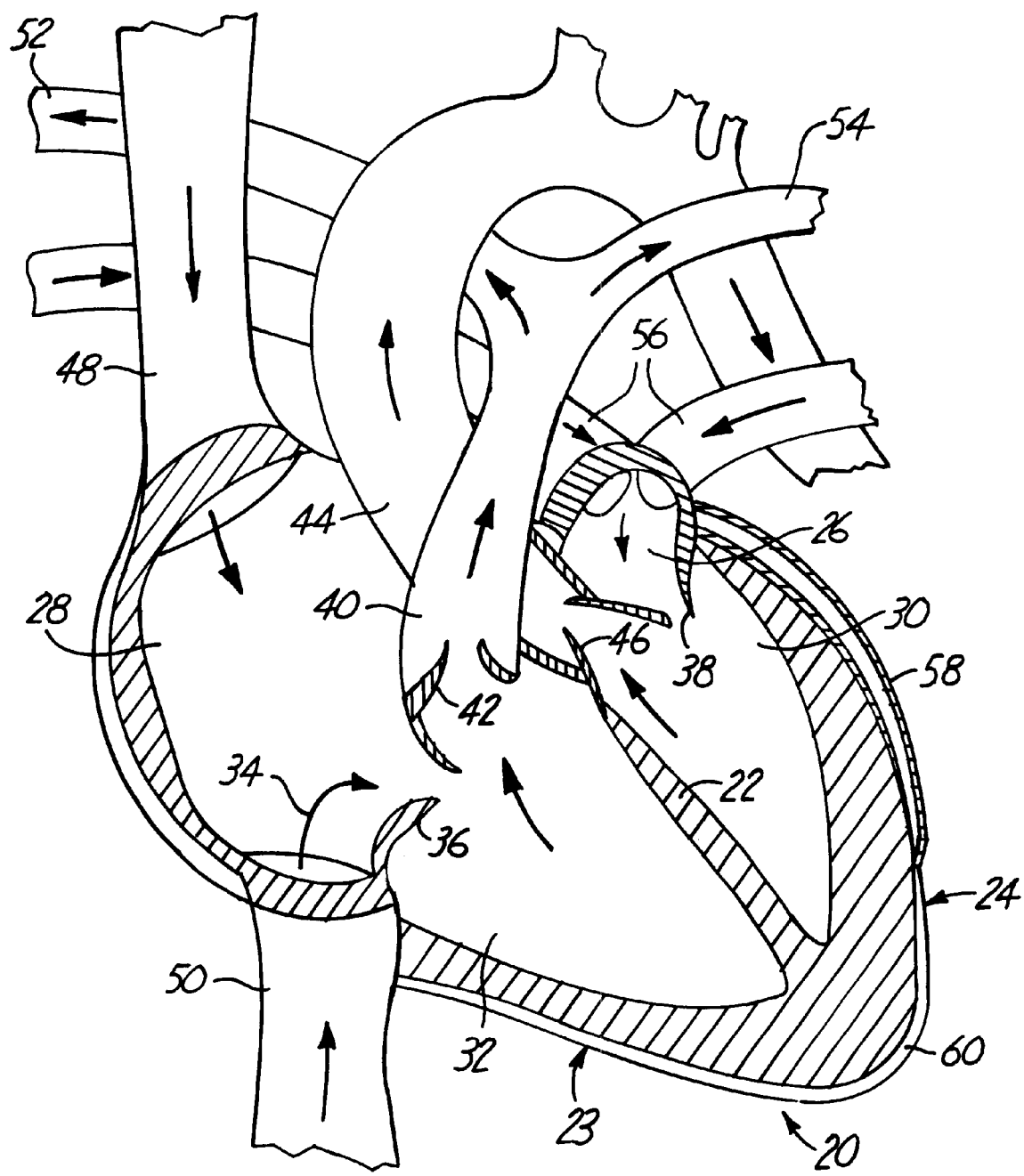
FIG. 1 illustrates a partial sectional view of a human heart and its associated proximate vascular system.

FIG. 1 illustrates a partially sectioned view of a human heart 20, and its associated vasculature. The heart 20 is subdivided by muscular septum 22 into two lateral halves, which are named respectively right 23 and left 24. A transverse constriction subdivides each half of the heart into two cavities, or chambers. The upper chambers consist of the left and right atria 26, 28 which collect blood. The lower chambers consist of the left and right ventricles 30, 32 which pump blood. The arrows 34 indicate the direction of blood flow through the heart. The chambers are defined by the epicardial wall of the heart.

The right atrium 28 communicates with the right ventricle 32 by the tricuspid valve 36. The left atrium 26 communicates with the left ventricle 30 by the mitral valve 38. The right ventricle 32 empties into the pulmonary artery 40 by way of the pulmonary valve 42. The left ventricle 30 empties into the aorta 44 by way of the aortic valve 46.

The circulation of the heart 20 consists of two components. First is the functional circulation of the heart 20, i.e., the blood flow through the heart 20 from which blood is pumped to the lungs and the body in general. Second is the coronary circulation, i.e., the blood supply to the structures and muscles of the heart 20 itself.

The functional circulation of the heart 20 pumps blood to the body in general, i.e., the systematic circulation, and to the lungs for oxygenation, i.e., the pulmonic and pulmonary circulation. The left side of the heart 24 supplies the systemic circulation. The right side 23 of the heart supplies the lungs with blood for oxygenation. Deoxygenated blood from the systematic circulation is returned to the heart 20 and is supplied to the right atrium 28 by the superior and inferior venae cavae 48, 50. The heart 20 pumps the deoxygenated blood into the lungs for oxygenation by way of the main pulmonary artery 40. The main pulmonary artery 40 separates into the right and left pulmonary arteries, 52, 54 which circulate to the right and left lungs, respectively, oxygenated blood returns to the heart 20 at the left atrium 26 via four pulmonary veins 56 (of which two are shown). The blood then flows to the left ventricle 30 where it is pumped into the aorta 44, which supplies the body with oxygenated blood.

The functional circulation, however, does not supply blood to the heart muscle or structures. Therefore, functional circulation does not supply oxygen or nutrients to the heart 20 itself. The actual blood supply to the heart structure, i.e., the oxygen and nutrient supply, is provided by the coronary circulation of the heart, consisting of coronary arteries, indicated generally at 58, and cardiac veins. Coronary artery 58 resides closely proximate the endocardial wall of heart 24. FIG. 1 also illustrates that the heart wall is surrounded by a pericardial sac 60. Sac 60 surrounds the heart and contains it within interstitial fluid.

Figure 2:
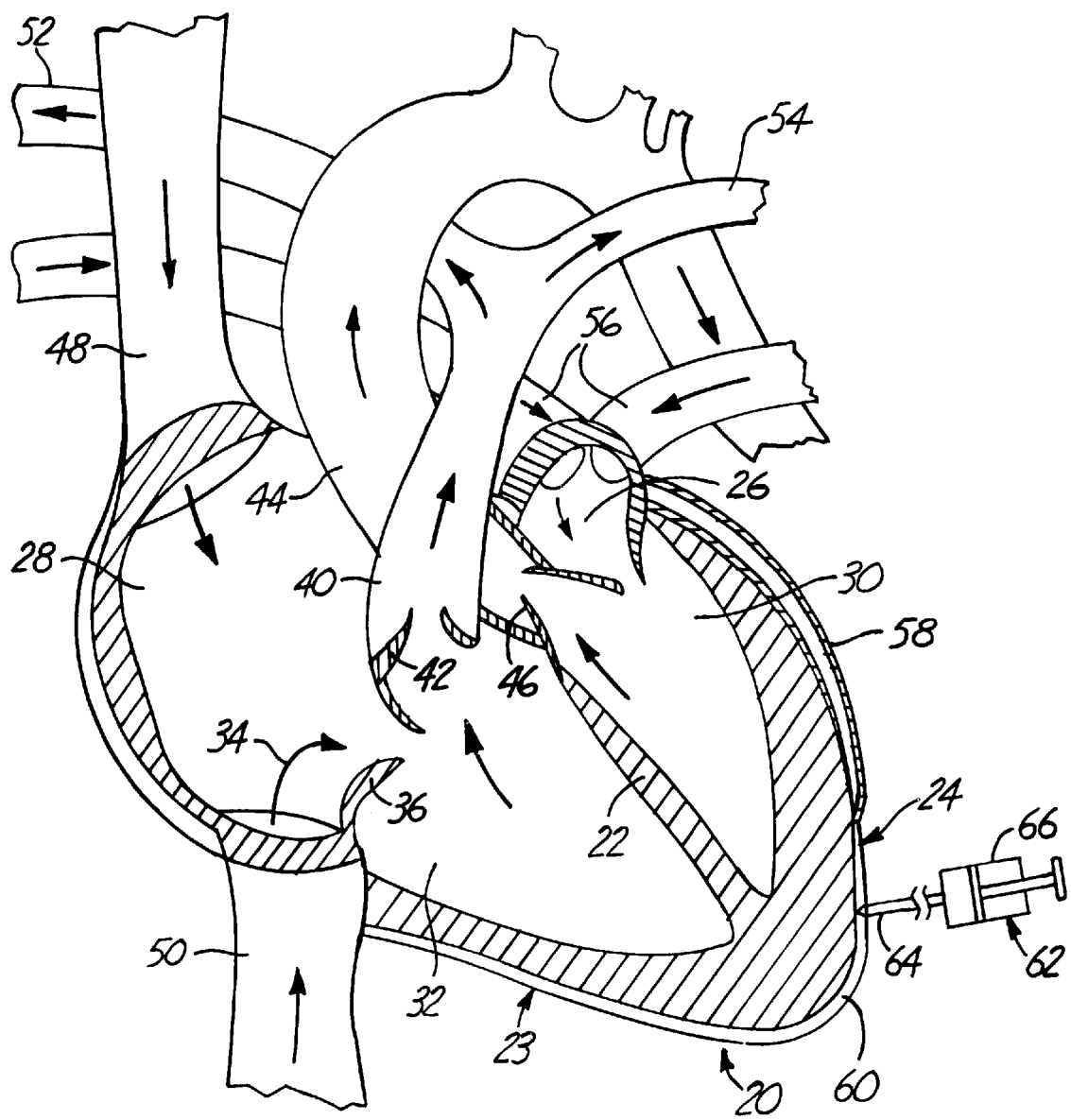
FIG. 2 illustrates the injection of an infusate or therapeutic agent into the pericardial sac of the heart illustrated in FIG. 1.

In accordance with one embodiment of the present invention, an iontophoretic technique is used to effect delivery of a therapeutic agent to the myocardial tissue. In FIG. 2, a needle 62 is illustrated having a shaft portion 64 and a barrel portion 66. It will be appreciated that, in accordance with one illustrative embodiment of the present invention, shaft 64 is injected into the body through the chest and has its distal tip placed within the pericardial sac 60. Needle 62 can be a conventional sternal needle, or it can be a low volume needle such as that described in co-pending U.S. patent application Ser. No. 09/138,131, which is hereby incorporated by reference.

In any case, needle 62 has its distal shaft 64 advanced into the pericardial sac 60 under fluoroscopy, or another suitable visualization technique. The physician then injects the therapeutic agent into the pericardial sac 60 by depressing the plunger in barrel 66. In one illustrative embodiment, the therapeutic agent is in either liquid or gel form and contains either positive or negative ions. Also, an electrode can be placed within the body having a portion thereof disposed within pericardial sac 60. The electrode, when energized, can assume a voltage potential which is relatively positive or negative. In addition, the shaft 64 of needle 62 can be electrically conductive and connected to a power supply to act as an electrode.

In one illustrative embodiment, the heart tissue around the entire periphery of the heart is to receive the therapeutic agent. In that case, enough of the therapeutic agent is injected into the pericardial sac 60 to bathe the heart in the therapeutic agent.

Figures 3A, 3B:
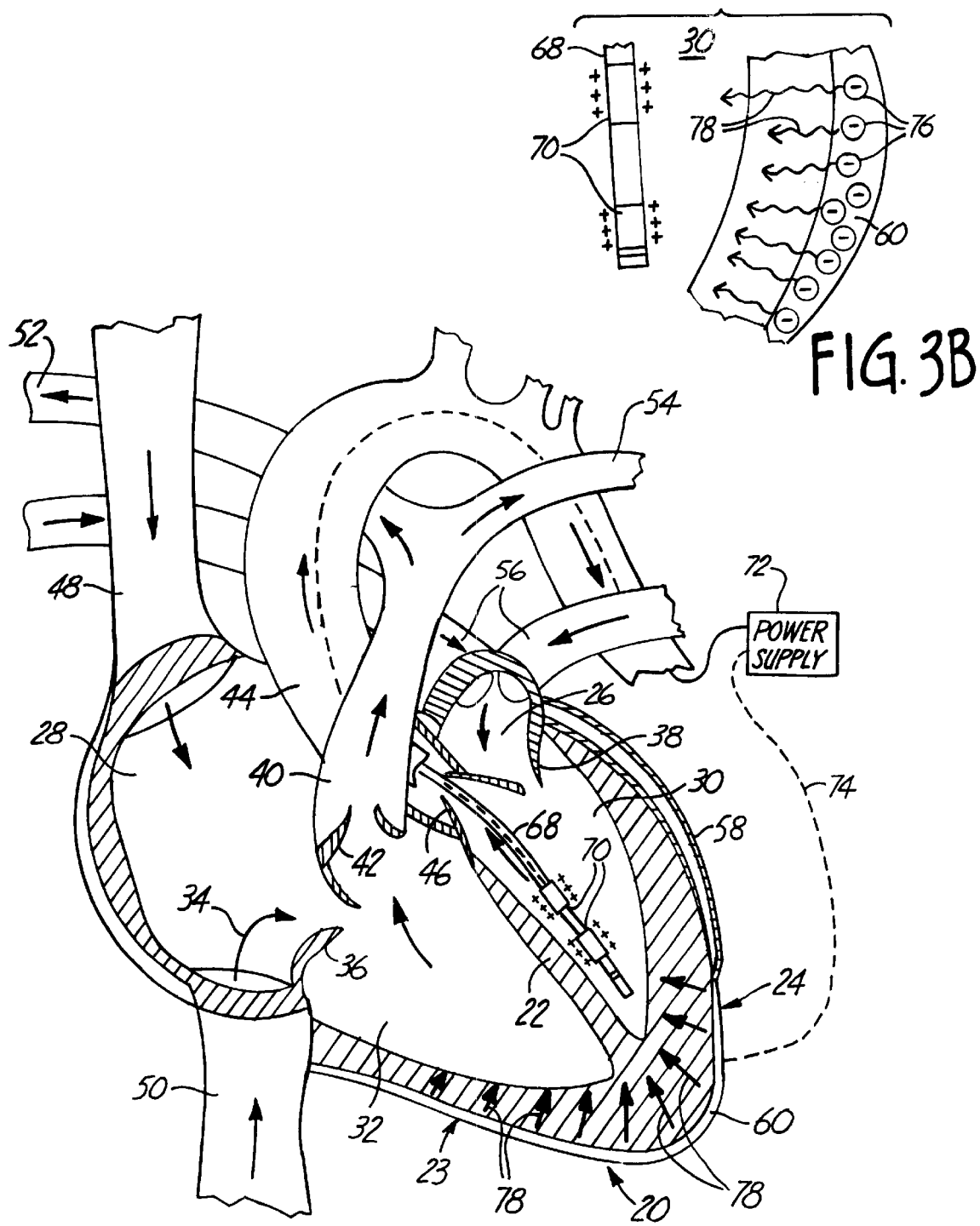
FIG. 3A illustrates the placement of an electrode in a heart chamber.
FIG. 3B is an enlarged view of a portion of the heart shown in FIG. 3A.

The next step in administering the therapeutic agent is illustrated in FIGS. 3A and 3B. FIG. 3A shows the heart 20 which has already had the therapeutic agent injected into pericardial sac 60. FIG. 3A also shows a catheter 68 which is introduced into heart chamber 30. In the illustrative embodiment, catheter 68 is introduced into left ventricle 30 through a guide catheter, or over a guide wire, or in another desirable manner.

Catheter 68 has an elongate portion with one or more electrodes 70 disposed thereon. Electrodes 70, which may illustratively be conductive sleeves or tabs, are coupled through a suitable conductor (such as a wire) back through, or along side, catheter 68 to power supply 72. Power supply 72 is energized to apply a constant low voltage to electrodes 70 to create either an anode or a cathode (depending upon the polarity of the therapeutic agent). Power supply 72 can have a second electrode located at least partially within pericardial sac 60. This is indicated by dashed line 74. In the illustrative embodiment, the therapeutic agent in pericardial sac either contains, or is energized to contain, negative ions.

When power supply 72 is energized, electrodes 70 achieve a positive voltage potential with respect to the negatively charged ions in the therapeutic agent within pericardial sac 60. The voltage potential created across electrodes 70 and an electrode 74 in pericardial sac 60 (or the ions in the therapeutic agent) sets up a field which interacts with the ionic therapeutic agent which acts to drive the ions in the therapeutic agent into the heart tissue in the heart wall between pericardial sac 60 and electrodes 70.

FIG. 3B is an enlarged view of a portion of the heart wall, therapeutic agent, and electrode 70 which are illustrated in FIG. 3A. FIG. 3B better illustrates that the therapeutic agent is provided with negative ions 76. When the voltage potential is set up across ions 76 and electrodes 70 and 74, the ions tend to migrate in the direction indicated by arrows 78, toward electrodes 70. This, of course, drives the ions into the heart tissue between pericardial sac 60 and the chamber 30 in which electrodes 70 reside. This driving force is the result of the well known iontophoretic technique.

Figure 4:
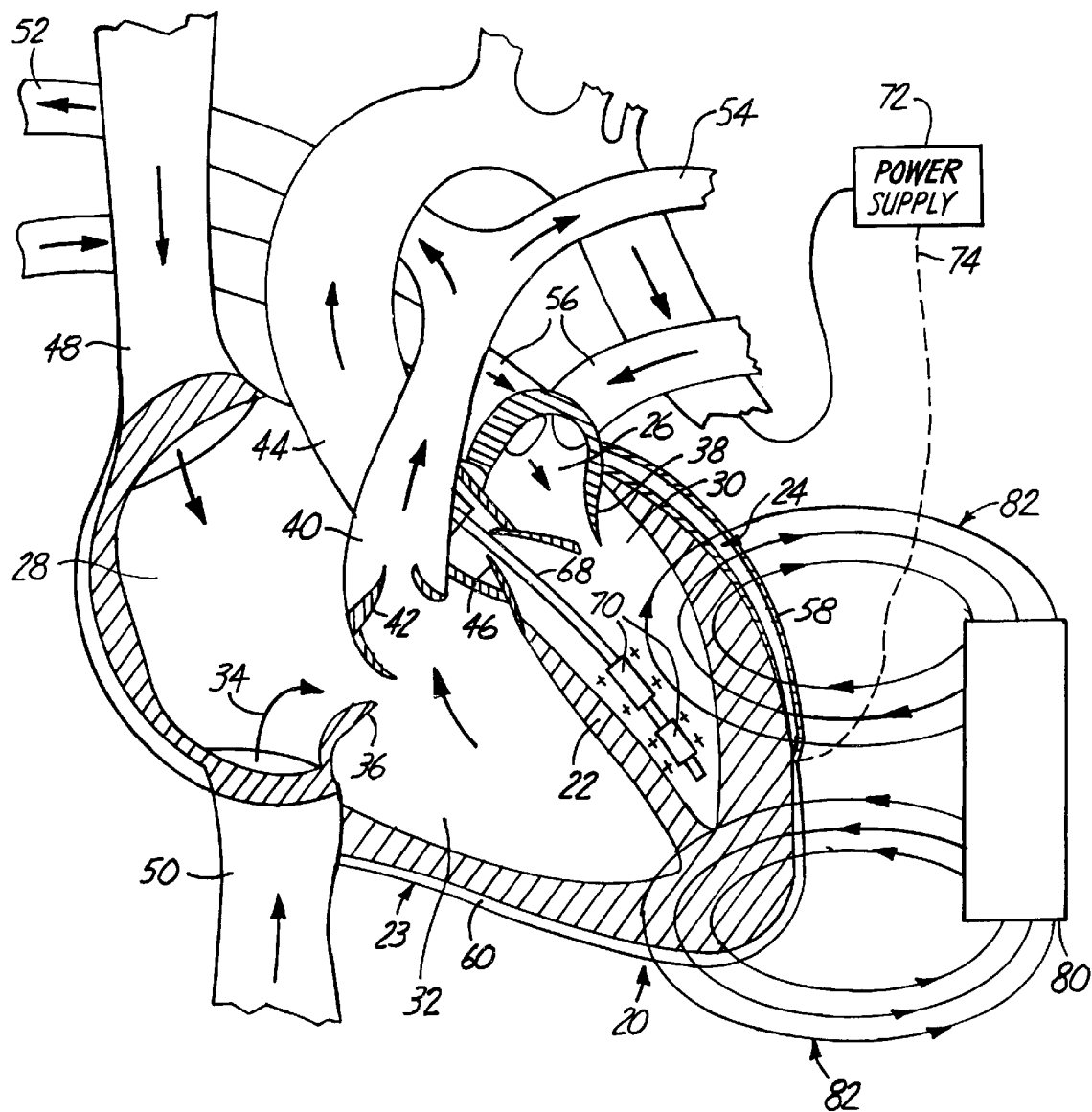
FIG. 4 illustrates the application of a force field generated by an external generator to assist in administering the therapeutic agent.

FIG. 4 illustrates another embodiment in accordance with one aspect of the present invention. In FIG. 4, a number of the elements are similar to those shown described with respect to FIG. 3, and are similarly numbered. However, FIG. 4 also illustrates a field generator 80. In one illustrative embodiment, field generator 80 is placed adjacent the body, and external to the body, proximate heart 20. Field generator 80 generates an electric or magnetic field illustrated by field lines 82 in FIG. 4. Electric or magnetic field 82 is oriented such that it assists in driving the ions from pericardial sac 60 into the heart tissue.

It can be seen that, depending on the size of the field 82, it can be used to enhance penetration of the ions into the heart tissue in a local area only in which the field lines are directing ion flow appropriately. This embodiment is illustrated in FIG. 4. However, it will be appreciated that a different size or shaped electric field can be generated such that a larger or smaller area of the heart tissue can be treated.

Figure 5:
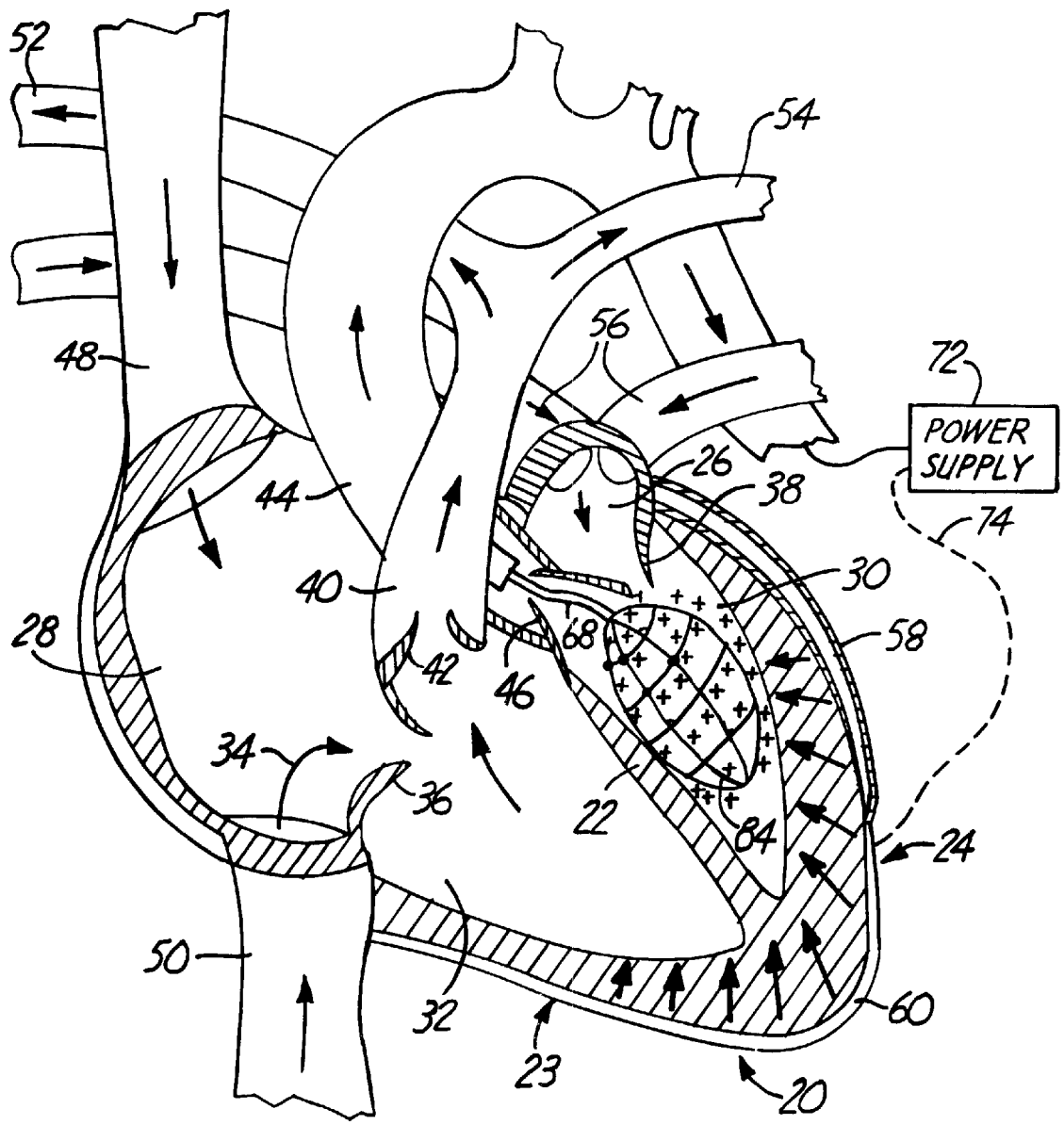
FIG. 5 illustrates an alternative embodiment of an electrode in accordance with one aspect of the present invention.

FIG. 5 illustrates yet another illustrative embodiment of the present invention. A number of items in FIG. 5 are similar to those in previous figures, and are similarly numbered. However, rather than showing two conductive strip or cylindrical electrodes 70, as are indicated in the previous figures, FIG. 5 illustrates a wire basket-shaped electrode 84. Basket-shaped electrode 84 is also delivered by catheter 68 which is similar to that which carries electrodes 70 described in FIGS. 3A and 3B.

However, electrode 84 is radially expandable and collapsible such that it can be delivered in a radially collapsed position through a guide catheter, or simply within the interior of catheter 88. In the radially expanded (or deployed) configuration, the wire portions of basket-shaped electrode 84 can be sized to press up against the heart tissue to be treated. This enhances the electric field in the area of the heart tissue near the electrode and enhances preferential migration of the ions in the therapeutic agent in pericardial sac 60 toward the desired area of heart tissue to be treated (i.e., toward electrode 84).

Basket-shaped electrode 84 can be formed of woven wires which are bonded to one another through adhesive, welding, or another suitable connection technique. Electrode 84 can also be shaped such that it has sufficient resilience to expanded to the expanded position once it exits catheter 68. Therefore, electrode 84 can be attached to a push rod or wire that extends proximally through catheter 68. During maneuvering of catheter 68 through the vasculature, electrode 84 is disposed within catheter 68 in the collapsed position.

However, once the distal tip of catheter 68 is within the desired heart chamber (such as heart chamber 30), catheter 60 can be retracted to expose electrode 84, or electrode 84 can be advanced from within catheter 68, as desired. In either case, once electrode 84 has emerged from the distal tip of catheter 68, electrode 84 self expands to assume the expanded position. Of course, electrode 84 can be expandable through a push-pull type manipulation mechanism, or any other mechanical, electrical, or electromechanical technique.

In one illustrative embodiment, each of the nodes (or crossing points) on basket-shaped electrode 84 is independently addressable by an external microprocessor, microcontroller or switch. The individually addressable nodes can be selectively energized to different potentials. Thus, this can create a shaped field which is preferentially higher in a certain area, to target a certain area of the heart tissue for greater ionic transfer.

It should also be noted that electrode 84 can be formed in any of a wide variety of different shapes and sizes. Such shapes and sizes will change with application and with the desired preferential migration of the therapeutic agent into the heart wall. When provided with appropriate marker bands (such as in a selected pattern, so that rotational orientation of the electrode can be seen under visualization) the electrode can be positioned to induce more strongly directed migration of the therapeutic agent into desired heart tissue.

It will also be noted that the particular shape of the electrode can serve to shape the electric field generated by the electrode, to some degree. This can be used to control the direction of preferential migration of the ions into the heart tissue. Thus, the therapeutic agent can be administered more preferentially to the region of the heart tissue for which the therapeutic agent is intended.

Figure 6:
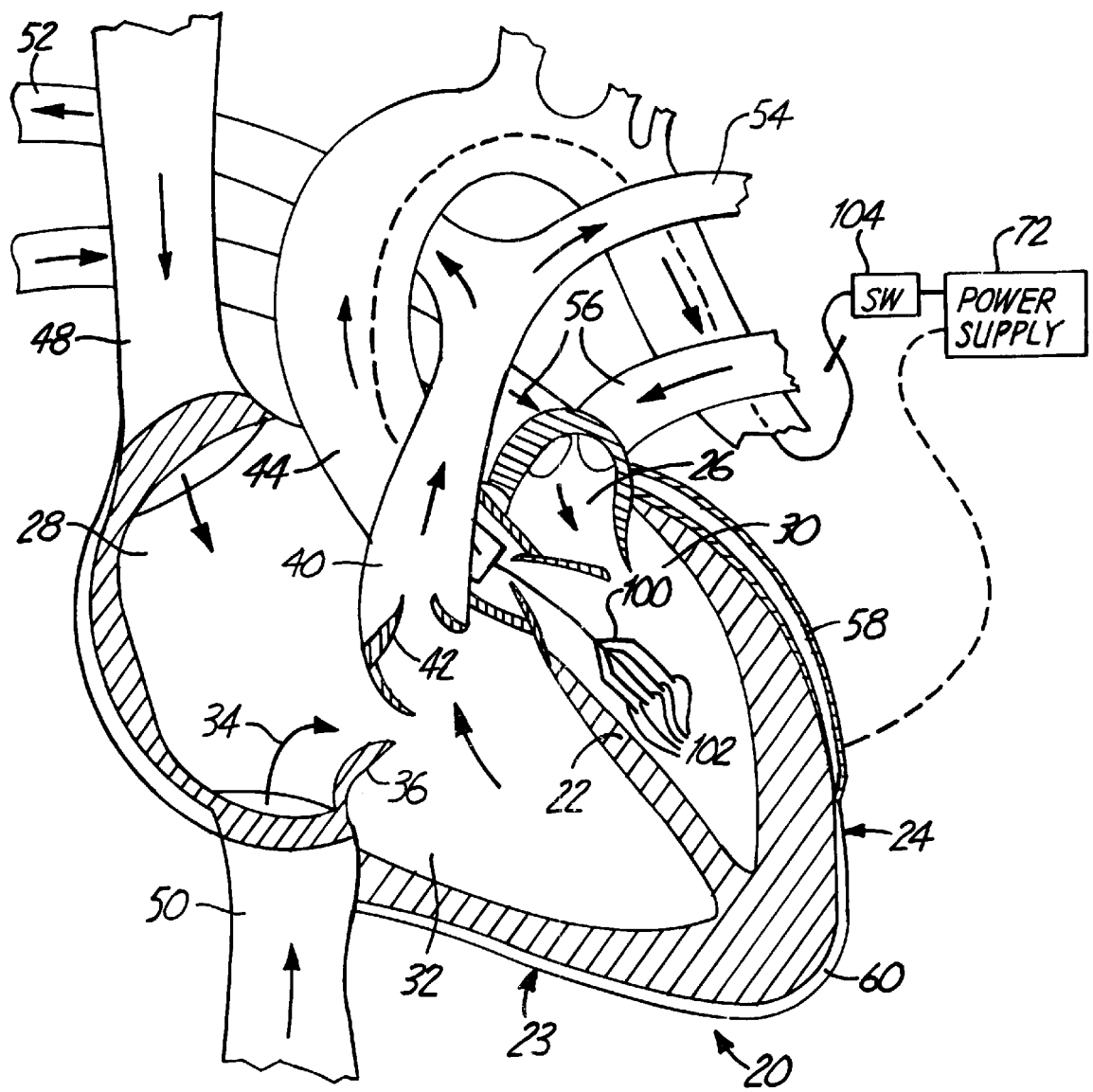
FIG. 6 illustrates an alternative embodiment of an electrode in accordance with one aspect of the present invention.

FIG. 6 illustrates another embodiment of an electrode 100 in accordance with one aspect of the present invention. Electrode 100 is actually formed of a plurality of different electrodes 102. Each of those electrodes is connected to power supply 72 through a switch 104. It will be appreciated that, while switch 104 is shown external to the vasculature and adjacent power supply 72, switch 104 can also be implemented as a semiconductor switch which resides somewhere along the catheter supporting electrodes 102 within the vasculature, or at the distal end of that catheter.

In any case, under certain circumstances, electrodes can become coated with material or gases which reduce the efficiency of the electrode. Similarly, during operation, the performance of electrode can degrade for other reasons. This degradation in efficiency or performance can be sensed simply by measuring the impedance of the system or by measuring current flowing through the system. In either case, this can be overcome with the system illustrated in FIG. 6.

In that system, one of electrodes 102 are first energized for the iontophoretic transfer. When the performance of that electrode has sufficiently degraded, switch 104 is actuated (by a microcontroller, by hand, or by any other suitable actuation mechanism) and the first electrode 102 is deselected and a second electrode 102 is selected for energization. This process can continue until all electrodes 102 have been used, or until the desired iontophoretic transfer has been accomplished.

Figure 7:
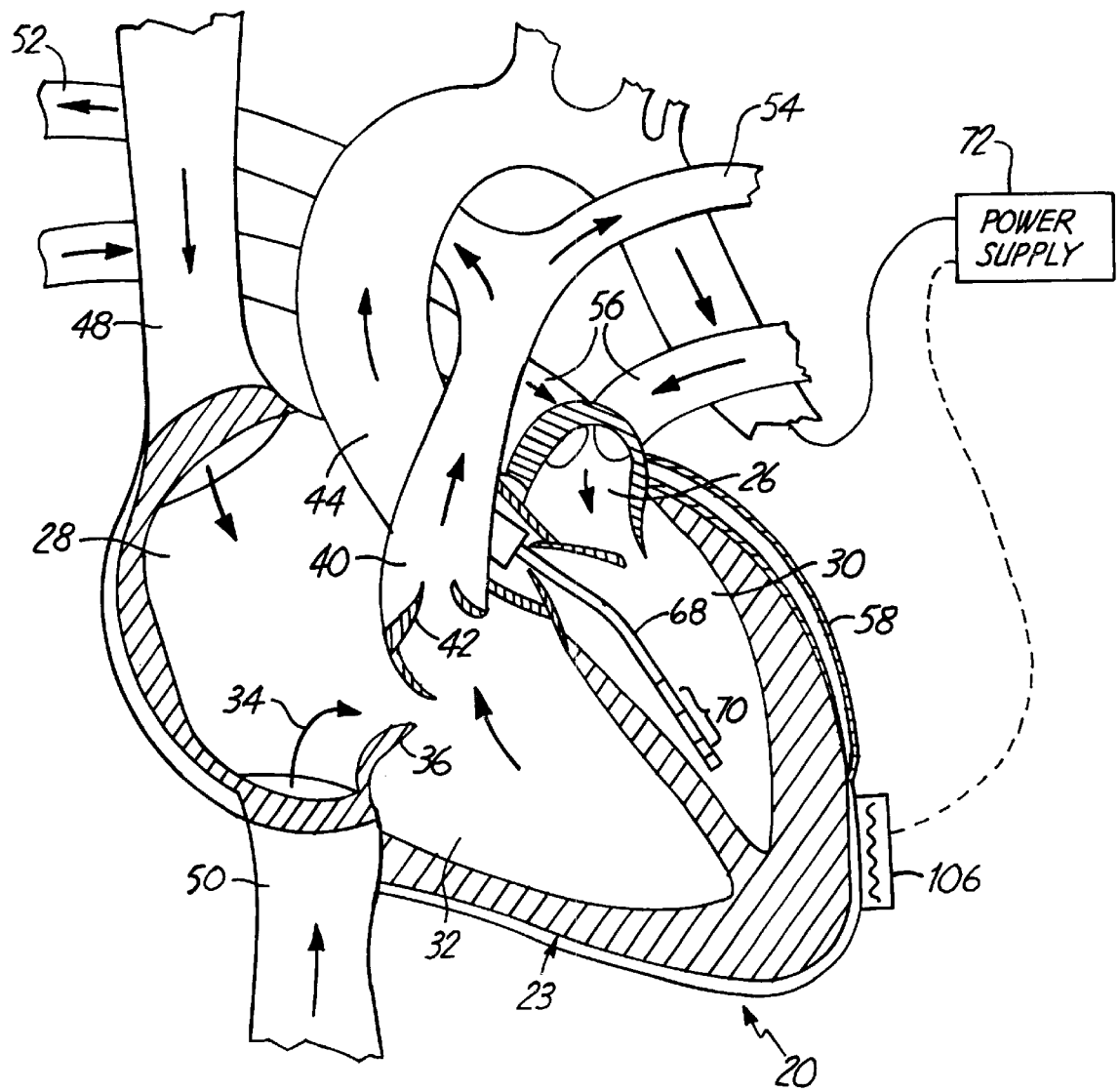
FIG. 7 illustrates an alternative embodiment of drug application in accordance with one aspect of the present invention.

FIG. 7 illustrates yet another embodiment of the present invention. While most of the present description has proceeded with respect to placing the drug to be transferred and one electrode in the paracardial sac, other embodiments are contemplated as well. For example, the drug can be placed inside the heart chamber and the polarity of the electrodes can be reversed to drive the drug through the heart muscle in an inside-out direction. Similarly, the drug can be administered systemically while a field is specifically created around the heart. As the drug is being transmitted through the blood stream, it will be preferentially transferred into the heart muscle where the field strength is the greatest.

Similarly, in some previous heart operations, paracardial sac 60 may be removed from the heart. In that case, the drug solution can be transferred to the heart muscle in a different way. For example, a patch 106 containing an ionic transport mechanism (such as hydrogel, etc.) can be percutaneously applied to the surface of the heart. Similarly, patch 106 can be inserted through a small hole in the chest and unfolded and then applied to the heart muscle. In any case, the drug to be transferred to the heart muscle is provided on one side of the heart muscle, and not necessarily within paracardial sac 60. The electrode on the other side of the heart muscle (and shown in FIG. 7 in the heart chamber) is then energized to create the necessary field for transfer of the drug into the heart muscle.

Figure 8:
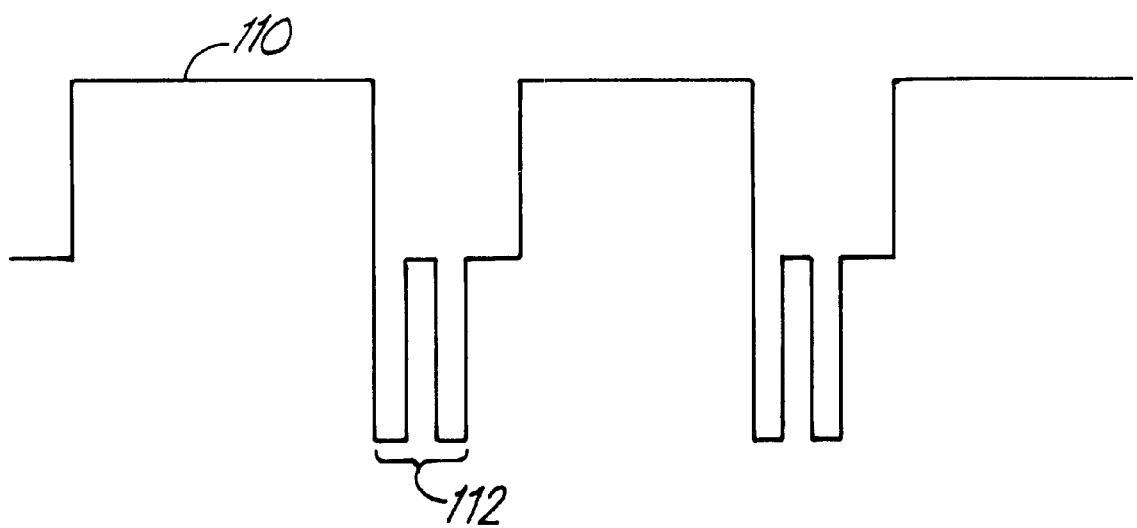
FIG. 8 is a waveform for signal application in accordance with one embodiment of the present invention.

As discussed above, when a DC current is used to implement the ionic transfer, electrodes can become coated with material or gases which reduces the efficiency of the ionic transfer. Thus, the signal on the electrodes can have a wave shape, such as that illustrated in FIG. 8. The wave shape has a first portion 110 which is substantially a DC current application. However, a second portion 112 of the wave shape reverses polarity for one or more fairly short time intervals. This waveform is repeated. Switching polarity on the electrodes has the effect of removing the coating gases or materials to thereby re-establish increased efficiency or performance of the electrodes. The specific duration for each of the pulses in the wave shape illustrated in FIG. 8 will, of course, be dependent on the ionic state of the drug itself, how much drug is being transported, etc.

Although the present invention has been described with reference to preferred embodiments, workers skilled in the art will recognize that changes may be made in form and detail without departing from the spirit and scope of the invention.

What is claimed is:

1. An apparatus for delivering a therapeutic agent to heart tissue in a body the apparatus comprising:
   a first electrode instrument including:
      an intravascular catheter including an elongate shaft having a proximal end and a distal end;
      a first electrode coupled to the distal end of the elongate shaft of the intravascular catheter and insertable therewith to form the first electrode instrument wherein the elongate shaft is configured to be introduced and advanced through vasculature in the body and positioned in a heart chamber
   a second electrode instrument including a second electrode coupleable to a percutaneous needle operable to inject the therapeutic agent proximate to the heart tissue in the body; and
   an instrument interface coupleable to a power source and configured to supply a first potential to the first electrode and a second potential to the second electrode and the first and second potentials having a potential difference to induce migration of the therapeutic agent injected proximate to the heart tissue.

2. The apparatus of claim 1 wherein the first electrode instrument comprises:
an expandable member, expandable in a generally radial direction from a contracted position to an expanded position and the first electrode is coupled to the expandable member and expandable therewith.

3. The apparatus of claim 1 wherein the first electrode instrument comprises:
a plurality of selectively energizable electrode members.

4. The apparatus of claim 3 and further comprising:
a switch operably coupled to the plurality of electrode members to select one of the plurality of electrode members.

5. The apparatus of claim 3 wherein the plurality of electrode members are coupled to an expandable member and are expandable therewith.

6. The apparatus of claim 5 wherein the plurality of electrode members are radially and longitudinally arranged.

7. The apparatus of claim 1 and wherein:
the needle of the second electrode instrument includes a conductive shaft portion coupleable to the power source to form the second electrode.

8. The apparatus of claim 1 wherein the needle is configured for insertion into a pericardial sac of the heart.

9. The apparatus of claim 1 wherein the needle includes a barrel portion for containing the therapeutic agent.

10. An apparatus for delivering a therapeutic agent to heart tissue in a body comprising:
an intravascular catheter including an elongate member having a proximal end and a distal end;
an intravascular electrode coupled to the distal end of the elongate member wherein the elongate member is configured to be introduced and advanced through vasculature in the body and positioned in a heart chamber;
an extravascular electrode and the intravascular electrode and the extravascular electrode being coupleable to a power source;
the extravascular electrode and the intravascular electrode being energizable to provide a potential difference between the extravascular electrode and the intravascular electrode to induce migration of the therapeutic agent; and
a subcutaneous delivery patch containing the therapeutic agent.

11. In combination:
a first instrument comprising:
an extravascular therapeutic agent delivery device and a first electrode coupled to the extravascular therapeutic agent delivery device; and
a second instrument comprising:
an intravascular catheter including an elongated catheter shaft and a second electrode carried by the intravascular catheter and insertable into a body vessel with the intravascular catheter;
an instrument interface coupleable to a power source and configured to supply a first potential to the first electrode of the first instrument and a second potential to the second electrode of the second instrument and the first and second potentials having a potential difference.

* * * * *